United States Patent [19]

Hirsenkorn

[11] Patent Number: 5,171,878
[45] Date of Patent: Dec. 15, 1992

[54] PROCESS FOR THE PREPARATION OF β-RESORCYLIC ACID DERIVATIVES

[75] Inventor: Rolf Hirsenkorn, Grosshesselohe, Fed. Rep. of Germany

[73] Assignee: Consortium for elektrochemische Industrie GmbH, Munich, Fed. Rep. of Germany

[21] Appl. No.: 649,895

[22] Filed: Feb. 4, 1991

[30] Foreign Application Priority Data

Mar. 15, 1990 [DE] Fed. Rep. of Germany ....... 4008223

[51] Int. Cl.$^5$ .............................................. C07C 69/76
[52] U.S. Cl. ...................................... 560/64; 560/70; 549/328
[58] Field of Search ..................... 560/64, 70; 549/328

[56] References Cited

U.S. PATENT DOCUMENTS

| | | | |
|---|---|---|---|
| 3,833,677 | 9/1974 | Grard | 560/64 |
| 4,020,098 | 4/1977 | Gosteli | 560/70 |
| 4,309,563 | 1/1982 | Suzuki | 560/64 |
| 4,339,593 | 7/1982 | Willis | 560/64 |
| 4,408,059 | 10/1983 | Smith, III | 560/64 |
| 4,420,629 | 12/1983 | Schmidt | 560/70 |
| 4,426,332 | 1/1984 | Thoemel | 560/70 |
| 4,524,216 | 6/1985 | Schmidt | 560/70 |
| 5,025,036 | 6/1991 | Carson | 560/64 |

FOREIGN PATENT DOCUMENTS 64605 11/1982 European Pat. Off. .
133960 3/1985 European Pat. Off. .
2653177 5/1978 Fed. Rep. of Germany .

*Primary Examiner*—Paul J. Killos
*Attorney, Agent, or Firm*—Collard & Roe

[57] ABSTRACT

Process for the preparation of β-resorcylic acid derivatives of the general formula

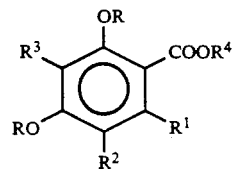

in which R, $R^2$ and $R^3$ can be identical or different and denote a hydrogen atom or an alkyl radical and $R^1$ and $R^4$ can be identical or different and denote an alkyl radical, by reaction of a diketone with β-ketocarboxylic acid derivatives in the presence of an alkaline earth metal compound. The derivatives are useful as fragrances, or in perfumes.

9 Claims, No Drawings

PROCESS FOR THE PREPARATION OF β-RESORCYLIC ACID DERIVATIVES

BACKGROUND OF THE INVENTION

1. Field of the Invention

The invention relates to a process for the preparation of β-resorcylic acid derivatives and the use of certain β-resorcylic acid derivatives as a fragrance or in perfumes.

2. The Prior Art

Processes for the preparation of β-resorcylic acid derivatives are already known. U.S. Pat. No. 3,944,596, granted to Cohen, describes a process for the preparation of resorcylic acid mono- and dialkylesters in which the corresponding dihydroresorcyclic acid esters are reacted with N-halogenoamides as aromatizing agents. A similar process is disclosed in U.S. Pat. No. 4,142,053, granted to Klein, according to which the dihydro-β-resorcylic acid esters are aromatized by heating with acetic anhydride/sulfuric acid to form diacetates, and these diacetates are hydrolyzed under alkaline or acid conditions in an additional reaction stage. These processes have the disadvantage that the accessibility of the starting substances is relatively difficult and, as a rule, additional synthesis steps are required.

β-Resorcylic acid esters can, furthermore, be prepared in accordance with U.S. Pat. No. 4,420,629, granted to Schmidt, by reaction of α-pyronyl-6-acetic acid esters with a base, the α-pyronyl-acetic acid esters being prepared in accordance with German Patent No. 2,916,648. This process has the disadvantage that it likewise comprises several stages and starts from educts which are not readily accessible.

A process for the preparation of β-resorcylic acid-6-alkyl esters by reaction of diketene (4-methylene-2-oxetanone) with β-ketocarboxylic acid esters and sodium hydride in a molar ratio of 1:1:1 is furthermore known from a publication by Tetsuzo Kato and Toyaharu Hozumi in Chem. Pharm. Bull. 20, 7 (1972) 1574-8. This process leads to only low yields and also has the disadvantage that the sodium hydride used as the catalyst is difficult to handle.

SUMMARY OF THE INVENTION

It is an object of this invention to provide a process which enables β-resorcylic acid derivatives to be prepared in a relatively simple manner and in a high yield.

The above object is accomplished in accordance with the present invention by providing a process for the preparation of β-resorcylic acid derivatives of the formula (1)

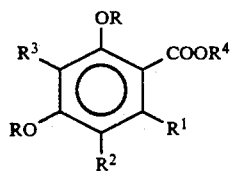

in which R, $R^2$ and $R^3$ can be identical or different and denote a hydrogen atom or an alkyl radical and $R^1$ and $R^4$ can be identical or different and denote an alkyl radical, by reacting a diketene of the formula (II)

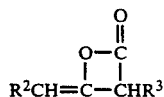

in which $R^2$ and $R^3$ have the above-mentioned meaning, with β-ketocarboxylic acid derivatives of the formula (III)

in which $R^1$ and $R^4$ have the above-mentioned meaning, in the presence of an alkaline earth metal compound.

DETAILED DESCRIPTION OF PREFERRED EMBODIMENT

Those diketenes of the formula (II) in which $R^2$ and $R^3$ can be identical or different and denote a hydrogen atom or an alkyl group having 1 to 5 carbon atoms are preferably employed in the process according to the invention.

Examples of hydrocarbon radicals having 1 to 5 carbon atoms are methyl, ethyl, n-propyl, iso-propyl, 1-n-butyl, iso-butyl, 2-n-butyl, tert.-butyl, n-pentyl, isopentyl, tert.-pentyl and neo-pentyl radicals.

Diketenes of the formula (II) in which $R^2$ and $R^3$ can be identical or different and denote a hydrogen atom or an alkyl group having 1 to 3 carbon atoms, in particular, a hydrogen atom or the methyl radical, are particularly preferably employed in the process according to the invention.

Examples of radicals R are the radicals mentioned for the radicals $R^2$ and $R^3$.

Preferred radicals R are the hydrogen atom and the methyl and ethyl radical, the hydrogen atom and the methyl radical being particularly preferred.

Examples of the diketenes according to formula (II) which are employed in the process according to the invention are

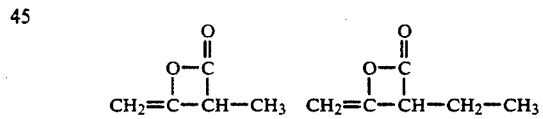

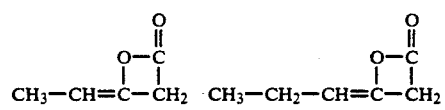

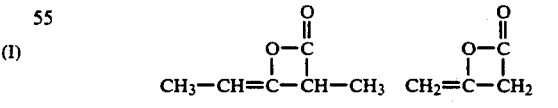

and

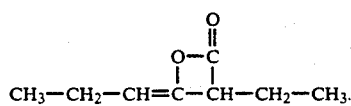

Examples of the diketenes which are particularly preferably employed in the process according to the invention are

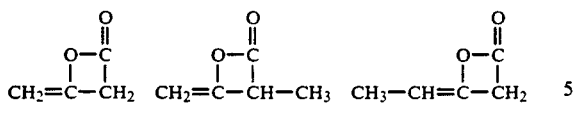

and

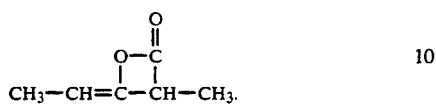

The diketenes employed according to the invention can be a single type of diketene. However, they can also be a mixture of at least two types of such diketenes.

The diketenes employed according to the invention can be prepared by processes which are known per se. Reference may be made in this context, for example, to U.S. Pat. No. 2,238,826, and to J.D. Roberts, J. Am. Chem. Soc. 71 (1949) 843-7.

The diketenes employed in the process according to the invention are preferably prepared by reacting a carboxylic acid halide of the formula (IV)

$$R^5-CH_2-\overset{\overset{O}{\|}}{C}-X \qquad (IV)$$

in which X denotes a halogen atom, such a fluorine, chlorine, bromine or iodine, particularly preferably chlorine, and $R^5$ has one of the meanings of $R^2$ or $R^3$, in the presence of a base, such as, for example, triethylamine, pyridine, N-methylmorpholine or diisopropylethylamine, particularly preferably triethylamine. The carboxylic acid halide employed here can be a single type of a carboxylic acid halide or a mixture of at least two types of such carboxylic acid halides.

Although not shown in formula (III), the β-ketocarboxylic acid derivatives employed can also be derivatives such as, for example, those of the general formulae

where $R^1$ and $R^4$ have one of the above-mentioned meanings, in which case the product obtained by the reaction according to the invention then subsequently also has to be converted into a β-resorcylic acid derivative according to the formula (I).

Those β-ketocarboxylic acid derivatives of the formula (III) in which $R^1$ and $R^4$ can be identical or different and denote an alkyl group having 1 to 5 carbon atoms are preferably employed in the process according to the invention.

Examples of the radicals $R^1$ and $R^4$ are all the examples mentioned for the radicals $R^2$ and $R^3$.

β-ketocarboxylic acid derivatives of the general formula (III) in which $R^1$ and $R^4$ can be identical or different and denote an alkyl group having 1 to 3 carbon atoms, in particular, the methyl radical, are particularly preferably employed in the process according to the invention.

Examples of the β-ketocarboxylic acid derivatives according to the formula (III) employed in the process according to the invention are

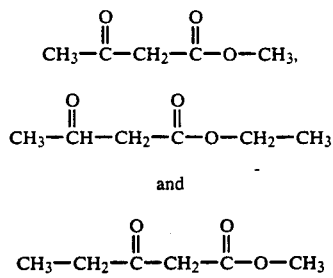

and

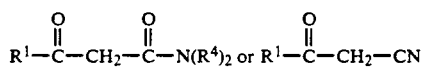

The β-ketocarboxylic acid derivative which is particularly preferably employed in the process according to the invention is

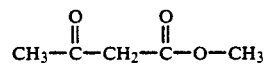

The, β-ketocarboxylic acid derivatives employed according to the invention can be a single type of a β-keto-carboxylic acid derivative. However, they can also be a mixture of at least two types of such β-ketocarboxylic acid derivatives.

The β-ketocarboxylic acid derivatives employed in the process according to the invention are commercially available products or can be prepared by methods customary in organic chemistry. Reference may be made in this context, for example, to G. Hesse. in Houben-Weyl, Methoden der organischen Chemie, "Enole"; Thieme Verlag, Stuttgart, 1968, 4th edition, Volume VI/1d, page 73 et seq. and E.J. Roskamp, J. Org. Chem. 54 (1989) 3258-60.

The alkaline earth metal compound in the process according to the invention is preferably an organic or inorganic compound of magnesium, calcium, strontium or barium.

Examples of the alkaline earth metal compounds employed in the process according to the invention are alkaline line earth metal hydroxides, such as $Mg(OH)_2$, $Ca(OH)_2$, $Sr(OH)_2.xH_2O$ and $Ba(OH)_2.xH_2O$, alkaline earth metal oxides, such as $MgO.xH_2O$ and CaO, alkaline earth metal carbonates, such as $MgCO_3$, $MgHCO_3$, $CaCO_3$, $SrCO_3$ and $BaCO_3$, and alkaline earth metal alcoholates, such as, for example, $Mg(OC_2H_5)_2$.

The alkaline earth metal compound employed according to the invention is particularly preferably an alkaline earth metal oxide or alkaline earth metal hydroxide, in particular, calcium oxide or calcium hydroxide.

The alkaline earth metal compound employed according to the invention can be a single type of an alkaline earth metal compound. However, it can also be a mixture of at least two types of such alkaline earth metal compounds.

In the process according to the invention, the molar ratio of diketene according to formula (II) to β-ketocarboxylic acid derivative according to formula (III) to alkaline earth metal compound in the reaction mass is preferably 1:1:1. However, the molar ratio of diketene according to formula (II) to β-ketocarboxylic acid derivative according to formula (III) to alkaline earth metal compound can also deviate slightly from the stoichiometric ratio of 1:1:1.

The process according to the invention can be carried out in the presence or in the absence of solvents, and the use of organic solvents which are inert with respect to the reaction mass being preferred.

Examples of solvents are alcohols, such as methanol, ethanol, n-propanol, iso-propanol, n-, sec.- and tert.-butanol, 2-butanol and ethylene glycol; esters, such as methyl acetate, ethyl acetate, n- and iso-propyl acetate, n-, sec.-and tert.- butyl acetate and ethyl formate; ethers, such as dioxane, tetrahydrofuran, diethyl ether, di-n-propyl ether, diisopropyl ether, di-n-butyl ether, ethylene glycol diethyl ether, ethylene glycol dimethyl ether, diethylene glycol dimethyl ether, diethylene glycol diethyl ether, diethylene glycol dibutyl ether and anisole; chlorinated hydrocarbons, such as methylene chloride, chloroform, carbon tetrachloride, 1,2-dichloroethane, 1,1,1-trichloroethane, trichloroethylene, tetrachloroethylene and chlorobenzene; hydrocarbons, such as pentane, n-hexane, hexane isomer mixtures, cyclohexane, heptane, octane, wash benzine, petroleum ether, benzene, ethyl benzene, toluene and xylenes; ketones, such as acetone, methyl ethyl ketone and methyl isobutyl ketone: dimethylformamide, dimethyl sulfoxide and mixtures of these solvents, ethers and ether-containing solvent mixtures, in particular, tetrahydrofuran and ethylene glycol dimethyl ether, being particularly preferred.

The term solvent does not mean that all the reaction components have to dissolve in it. The reaction can also be carried out in a suspension or emulsion of one or more reactants.

Solvents are preferably employed in the process according to the invention in amounts of 40 to 90% by weight, particularly preferably 60 to 70% by weight, in each case based on the total weight of the reaction mass.

The process according to the invention is preferably carried out at a temperature between 0° and 200° C., particularly preferably at the boiling point of the solvent used, under a pressure of between 900 and 1,100 hPa. If desired, higher or lower pressures can also be used.

The diketene according to formula (II), $\beta$-ketocarboxylic acid derivative according to formula (III), alkaline earth metal compound and, if appropriate, solvent are mixed in any desired manner in the process according to the invention.

The $\beta$-resorcylic acid derivative according to formula (I) where R is an alkaline earth metal ion is, as a rule, obtained in the process according to the invention, from which the $\beta$-resorcylic acid ester according to formula (I) where R is a hydrogen atom is obtained by acidification with an aqueous mineral acid, such as, for example, hydrochloric acid, sulfuric acid or phosphoric acid, or an organic acid, such as, for example acetic acid.

If the process according to the invention is carried out in an alkanol as the solvent, $\beta$-resorcylic derivatives in which some or all of the hydroxyl groups are etherified can be formed.

In a preferred embodiment of the process according to the invention, the $\beta$-ketocarboxylic acid derivative according to formula (III) is mixed with the equimolar amount of alkaline earth metal compound and solvent, the mixture is heated to the boiling point of the solvent and the equimolar amount, based on the amount of $\beta$-ketocarboxylic acid derivative employed, of diketene is added.

In a particularly preferred embodiment of the process according to the invention, an acetoacetic acid derivative is mixed with the equimolar amount of an alkaline earth metal oxide or alkaline earth metal hydroxide and solvent containing tetrahydrofuran and/or ethylene glycol dimethyl ether, the mixture is heated to the boiling point of the solvent containing tetrahydrofuran and/or ethylene glycol dimethyl ether and an equimolar amount, based on the amount of acetoacetic acid derivative employed, of a mixture of diketenes containing 4-methylene-2-oxetane and 3-methyl-4-methylene-2-oxetane is added, organic or inorganic acid being added after the reaction.

The $\beta$-resorcylic acid derivative according to formula (I) prepared by the process according to the invention can be recovered, isolated and purified by processes that are known per se, such as extraction, crystallization, distillation and extraction.

The process according to the invention has the advantage that the $\beta$-resorcylic acid derivatives of the formula (I) can be prepared in a simple manner in one synthesis step, it being possible for starting substances which are relatively readily accessible to be used.

The process according to the invention moreover has the advantage that $\beta$-resorcylic acid derivatives of the formula (I) are obtained in a high yield and with very good olfactory properties.

The $\beta$-resorcylic acid derivatives prepared according to the invention can be employed, in all cases, where $\beta$-resorcylic derivatives have also previously been employed. Thus, for example, they can be employed directly or as intermediates in the fields of pharmaceuticals, agrochemicals, perfumes and polymers.

Because of its characteristic oak moss smell, methyl 3,6-dimethyl-$\beta$-resorcylate is particularly suitable as a fragrance. Oak moss odoriferous substances are important constituents in perfumes having cypress and fern notes. It has been found that a mixture of methyl 3,6-dimethyl-$\beta$-resorcylate and methyl 6-methyl-$\beta$-resorcylate, which is distinguished by a mossy, woody, phenolic smell, is a very good odoriferous substance having an oak moss character.

Methyl 6-methyl-$\beta$-resorcylate is also suitable for the preparation of orcinyl, which can be used as an odoriferous substance having an oak moss character. Reference may be made, in this context, for example, to G. Nicollier, M. Rebetez, R. Tabacchi, Helv. Chim. Acta 61 Fasc. 8 (1978) No. 275, 2899–904. Methyl 6-methyl-$\beta$-resorcylate can moreover also be used for the preparation of methyl 4-acetoxy-6-methylacetylsalicylate, which is likewise known as an odoriferous substance having an oak moss character. Reference may be made, for example, in this context, to U.S. Pat. No. 3,884,843.

In the examples described below, all the parts and percentages are by weight, unless stated otherwise. Unless stated otherwise, the following examples are carried out under a pressure of the surrounding atmosphere, that is to say under about 1,000 hPa and at room temperature, that is to say at about 23° C., or at a temperature which is established when the reactants are brought together at room temperature without additional heating or cooling.

EXAMPLE 1

55.7 g (0.48 mol) of methyl acetoacetate are introduced into a suspension of 27.3 g (0.4s mol) of calcium oxide in 350 ml of tetrahydrofuran, and the mixture is heated to 50° C. and stirred for one hour. 40.3 g (0.48 mol) of 4-methylene-2-oxetane, which can be prepared in accordance with German patent No. 687,065, published Jan. 22, 1940, granted to Consortium für elektrochemische Industrie GmbH, are then slowly added dropwise, the mixture being cooled during the dropwise addition, so that the temperature of the reaction mixture does not exceed a value of 40° C. and lies between 30° C. and 40° C. The mixture is boiled under reflux for 8 hours and, after cooling to room temperature, the tetrahydrofuran is removed by distillation. 260 ml of methyl tert.-butyl ether are then added and 2N HCl is added to the resulting mixture in an amount such that the calcium oxide contained in the mixture dissolves. After extracting three times with methyl tert.-butyl ether, water is added to the organic phase, the aqueous phase is brought to pH 6 with NaOH (10% strength) and the mixture is extracted three times with methyl tert.-butyl ether. Removal of the solvent from the organic phase gives 77.3 g of pale brown crystals having a purity of 92% (gas chromatography), which corresponds to a yield of 83%, of the following structure

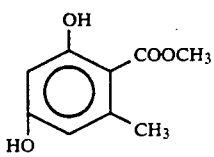

The smell of the methyl 6-methyl-β-resorcylate thus obtained can be described as follows: mossy, Woody, phenolic, oak moss character.

In the 200 MHz $^1$H-NMR spectrum in CDCl$_3$ and TMS as the internal standard, the resulting 6-methyl-β-resorcylic acid ester thus obtained exhibits signals at 11.75 (s, 1H, OH), 6.27 and 6.23 (d, 1H, $J_{3/5}=2$ Hz), 5.40 (br. s, 1H, OH), 3.92 (s, 3H, COOCH$_3$) and 2.48 (s, 3H, CH$_3$).

For further purification of the 6-methyl-β-resorcylic acid ester thus obtained, the product can be recrystallized from petrol ether/ethyl acetate.

The 6-methyl-β-resorcylic acid ester thus obtained can be further used, for example, as follows:

(a) Preparation of Orcinyl

A 18.55 g of the 6-methyl-β-resorcylic acid ester prepared according to the invention and 14.3 g of potassium carbonate (anhydrous) are initially introduced into acetone, 9.5 ml of methyl iodide in acetone are added dropwise, and the mixture is boiled under reflux for 12 hours. The acetone is then distilled off, the residue is acidified while cooling with ice, and the mixture is extracted three times with ethyl acetate. 15.71 g (yield: 79%) of methyl 4-methoxy-6-methyl-salicylate are obtained, the smell of which can be characterized as follows: sweet, earthy, walnut, mossy.

1.0 g of the methyl 4-methoxy-6-methyl-salicylate thus obtained is boiled under reflux with 35 ml of aqueous potassium hydroxide solution (15% strength) for 8 hours. The reaction mixture is then acidified with dilute hydrochloric acid and extracted with ethyl acetate. 0.70 g (yield: 70%) of orcinyl (3-methoxy-5-methylphenol) is obtained.

(b) Preparation of Methyl 4-acetoxy-6-methyl-acetylsalicylate 5 g of the 6-methyl-β-resorcylic acid ester prepared according to the invention, 11.2 g of acetic anhydride, 0.3 g of sodium acetate and 50 ml of xylene are heated at 135° C. for several hours, about 15 ml of an azeotrope being distilled over. The excess acetic anhydride and xylene are then distilled off under 20 mmHg. The residue is dissolved in 50 ml of toluene, and the organic phase is washed twice with saturated sodium carbonate solution and twice with water. The crystalline paste obtained after removal of the solvent is recrystallized from xylene/propanol. 5.2 g of methyl-4-acetoxy-6-methyl-acetylsalicylate (yield: 71%; melting point: 48° C.) are obtained.

EXAMPLE 2

(a) Preparation of Diketenes 647.7 g (7.0 mol) of propionyl chloride and 549.5 g (7.0 mol) of acetyl chloride are added dropwise to a mixture of 1,416.7 g (14 mol) of triethylamine in 15 liters of methyl tert.-butyl ether, whereupon the mixture heats up. After stirring at room temperature for 5 hours, the mixture thus obtained is cooled to a temperature of −15° C. and the triethylamine hydrochloride is then removed by filtration with suction. The solution which remains is concentrated to a volume of about 1 liter and then finely distilled through a 30 cm Vigreux column. 609.0 g of a mixture having the following composition are obtained, corresponding to a yield of 89%:

| | | |
|---|---|---|
| 4-methylene-2-oxetane (DIKE) | $\begin{array}{c} O \\ \parallel \\ O-C \\ \mid \quad \mid \\ CH_2=C-CH_2 \end{array}$ | (21.4%) |
| 3-methyl-4-methylene-2-oxetane (MEDIKE) | $\begin{array}{c} O \\ \parallel \\ O-C \\ \mid \quad \mid \\ CH_2=C-CH-CH_3 \end{array}$ | (29.7%) |
| 4-ethylidene-2-oxetane (I-MEDIKE) | $\begin{array}{c} O \\ \parallel \\ O-C \\ \mid \quad \mid \\ CH_3-CH=C-CH_2 \end{array}$ | (22.6%) |
| 3-methyl-4-ethylidene-2-oxetane (DIMEDIKE) | $\begin{array}{c} O \\ \parallel \\ O-C \\ \mid \quad \mid \\ CH_3-CH=C-CH-CH_3 \end{array}$ | (26.2%) |

In the 200 MHz $^1$H-NMR spectrum in CDCl$_3$, and TMS as internal standard, the diketenes thus obtained exhibit signals at:

DIKE: 4.80 (m, 1H$^{vin}$), 4.48 (m, 1H, H$^{vin}$), 3.88 (m, 2H, C$\underline{H}_2$CO) ppm, MEDIKE: 4.74 (dd, 1H, H$^{vin}$, $J_{gem.}=5$ Hz, $J_{all.}=1$ Hz), 4.47 (dd, 1H, H$^{vin}$, $J_{gem.}=5$ Hz, $J_{all.}=1$ Hz), 4.0 (q, 1H, C$\underline{H}$CH$_3$CO, J=8 Hz), 1.47 (d, 3H, CH$_3$, J=8 Hz) ppm,

| | |
|---|---|
| DIMEDIKE: | 4.75 (dq, 1H, H$^{vin}$, $J_{vic}=$ 7 Hz, $J_{all.}=1$ Hz), |
| | 3.98 (dq, 1H, C$\underline{H}$CH$_3$CO, $J_{vic}=$ 9.0 Hz, $J_{all.}=1$ Hz), |
| | 1.67 (dd, 3H, C$\underline{H}_3$—C═C, $J_{vic}=$ 7 Hz, $J_{homoall.}=1$ Hz), |
| | 1.41 (d, 3H, CHC$\underline{H}_3$CO, $J_{vic}=$ 9.0 Hz) ppm and |

I-MEDIKE: 4.75 (q, 1H, H$_{vin}$), 4.83 (m, 2H, C$\underline{H}_2$CO), 1.7 (d, 3H, C$\underline{H}_3$C═C, J=7.0 Hz) ppm.

The diketene mixture thus obtained is separated by distillation. The following fractions are obtained:

| Fraction | | Boiling Range (20 mm Hg) |
| --- | --- | --- |
| 1. | DIKE/MEDIKE | 40–44° C. |
| 2 | I-MEDIKE/DIMEDIKE | 46–51° C. |

(b) Preparation of β-Resorcylic Acid Derivatives 185.6 g (1.60 mol) of methyl acetoacetate are added to a suspension of 89.6 g (1.60 mol) of calcium oxide in 2.0 l of tetrahydrofuran, and the mixture is heated to 50° C. and stirred for one hour. 145.7 g (1.60 mol) of a mixture of 48 percent of DIKE and 52 percent of MEDIKE, the preparation of which is described above under (a), are then slowly added dropwise and the procedure is as described in Example 1. The solvent is removed from the organic phase, and the residue is subjected to fractional crystallization from 1 liter of toluene. 266.5 g of colorless crystals having a purity of 95% (gas chromatography), corresponding to a yield of 88%, of the following structure remain

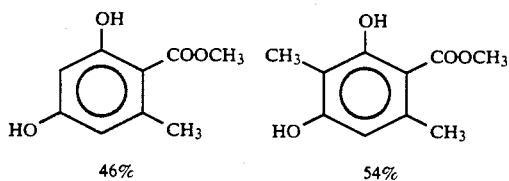

46%   54%

The smell of the resulting mixture of methyl 6-methyl-β-resorcylate and methyl 3,6-dimethyl-β-resorcylate can be described as follows: mossy, woody, phenolic. The mixture is particularly suitable as an odoriferous substance having an oak moss character. This mixture contains from 45% to 50% by weight of methyl 6-methyl-β-resorcylate and from 50% to 55% by weight of methyl 3,6-dimethyl-β-resorcylate.

In the 200 MHz $^1$H-NMR spectrum in CDCl$_3$ and TMS as internal standard, the methyl β-resorcylate mixture thus obtained exhibits signals for methyl 6-methyl-β-resorcylate at 11.75 s, 1H, OH), 6.27 and 6.23 (d, 1H, J$_{3/5}$=2 Hz), 5.40 (sb, 1H, OH), 3.92 (s, 3H, COOCH$_3$) and 2.48 (s, 3H, CH$_3$) ppm and for methyl 3,6-dimethyl-β-resorcylate at 12.05 (s, 1H, 2-OH), 6.22 (s, 1H, H$^5$), 5.19 (s, 1H, 4-OH), 3.92 (s, 3H, COOCH$_3$), 2.46 (s, 3H, 6-CH$_3$) and 2.10 (s, 3H, 3-CH$_3$) ppm.

For further purification of the mixture thus obtained, the product can also be recrystallized from toluene, methylene chloride or hexane.

EXAMPLE 3

185.6 g (1.60 mol) of methyl acetoacetate are added to a suspension of 89.6 g (1.60 mol) of calcium oxide in 2.0 liters of tetrahydrofuran, and the mixture is heated to 50° C. and stirred for 1 hour. 1.60 mol of a mixture of 49 percent of I-MEDIKE and 51 percent of DIMEDIKE, the preparation of which is described in Example 2 under (a), are then slowly added dropwise, and the procedure is as described in Example 1. The solvent is removed from the organic phase, and the residue is subjected to fractional crystallization from 1 liter of toluene. Colorless crystals of the following structure

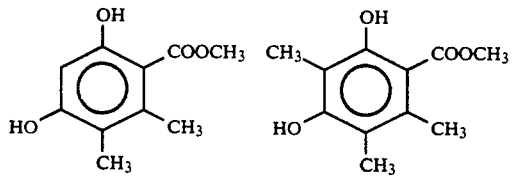

are obtained in a yield of 91 percent.

In the resulting mixture of methyl 5,6-dimethyl-β-resorcylate (balsamy, amber-like, fruity) and methyl 3,5,6-trimethyl-β-resorcylate (lovage, walnut, maple lactone), the lovage smell dominates. This mixture contains from 45% to 50% by weight of methyl 5,6-dimethyl-β-resorcylate and from 50% to 55% by weight of methyl 3,5,6-trimethyl-β-resorcylate.

In the 200 MHz $^1$H-NMR spectrum in CDCl$_3$ and TMS as internal standard, the methyl β-resorcylate mixture thus obtained exhibits signals for methyl 5,6-dimethyl-β-resorcylate at 11.26 (s, 1H, 2-OH), 6.27 (s, 1H, H$^3$), 5.60 (br. s, 1H, OH), 3.93 (s, 3H, COOCH$_3$), 2.45 (s, 3H, 6-CH$_3$) and 2.11 (s, 3H, 5-CH$_3$) ppm and for methyl 3,5,6-trimethyl-β-resorcylate at 11.46 (s, 1H, 2-OH), 5.15 (s, 1H, 4-OH), 3.91 (s, 3H, COOCH$_3$), 2.42 (s, 3H, 6-CH$_3$) and 2.13 (s, 6H, 3- and 5-CH$_3$) ppm. R$_f$ values (petrol ether/ethyl acetate 8:2) for methyl 5,6-dimethyl-β-resorcylate: 0.29 and for methyl 3,5,6-trimethyl-β-resorcylate: 0.40.

For further purification of the mixture thus obtained, the product can also be recrystallized from toluene, methylene chloride or hexane.

While only a few embodiments of the present invention has been shown and described, it is to be understood that many changes and modifications may be made thereunto, without departing from the spirit and scope of the invention as defined in the appended claims.

What is claimed is:

1. A process for the preparation of a β-resorcylic acid derivative of the formula (I)

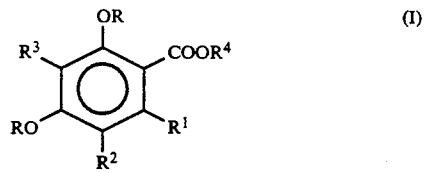

(I)

in which R, R$^2$ and R$^3$ can be identical or different and denote a hydrogen atom or an alkyl radical and R$^1$ and R$^4$ can be identical or different and denote an alkyl radical comprising:

reacting a diketene of the formula (II)

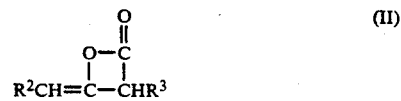

(II)

in which R$^2$ and R$^3$ have the above-mentioned meaning, with a β-ketocarboxylic acid derivative of the formula (III)

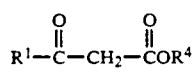

in which $R^1$ and $R^4$ have the above-mentioned meaning, and;
at a temperature between 0° and 200° C.,
under a pressure of between 900 and 1,100 hPa,
in the presence of alkaline earth metal compound.

2. The process as claimed in claim 1,
wherein $R^2$ and $R^3$ of the diketene of the formula (II) can be identical or different and denote a hydrogen atom or an alkyl group having 1 to 3 carbon atoms.

3. The process as claimed in claim 1,
wherein a diketene of the formula (II) is prepared by reaction of a carboxylic acid halide of the formula (IV)

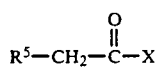

in which X denotes a halogen atom and $R^5$ has one of the meanings of $R^2$ or $R^3$, in the presence of a base.

4. The process as claimed in claim 1,
wherein $R^1$ and $R^4$ of the β-ketocarboxylic acid derivative of the formula (III) can be identical or different and denote an alkyl group having 1 to 3 carbon atoms.

5. The process as claimed in claim 1,
wherein said alkaline earth metal compound comprises an alkaline earth metal oxide.

6. The process as claimed in claim 1,
wherein said alkaline earth metal compound is calcium oxide.

7. The process as claimed in claim 1,
wherein said alkaline earth metal compound is an alkaline earth metal hydroxide.

8. The process as claimed in claim 1,
further comprising conducting the reaction in the presence of a solvent.

9. The process as claimed in claim 1,
comprising mixing an acetoacetic acid derivative with an equimolar amount of an alkaline earth metal oxide or alkaline earth metal hydroxide and a solvent selected from tetrahydrofuran containing solvent, ethylene glycol dimethyl ether containing solvent and mixtures thereof;
heating the mixture to the boiling point of the solvent selected from tetrahydrofuran containing solvent ethylene glycol dimethyl ether containing solvent and mixtures thereof; and
adding an equimolar amount, based on the amount of acetoacetic acid derivative employed, of a mixture of diketene containing 4-methylene-2-oxetane and 3-methyl-4-methylene-2-oxetane.

* * * * *